(12) United States Patent
Pappas et al.

(10) Patent No.: US 9,089,430 B2
(45) Date of Patent: Jul. 28, 2015

(54) PROSTHETIC ASSEMBLY

(75) Inventors: Christos Pappas, Agrinio (GR); Heikki Vilhelm Pitkanen, Helsinki (FI); Robert John Andrew Bigsby, Penarth (GB); Esa Taplo Anttila, Espoo (FI); Anthony Ward, Westbury-On-Trym (GB)

(73) Assignee: Biomet UK Limited, South Wales (GB)

( * ) Notice: Subject to any disclaimer, the term of this patent is extended or adjusted under 35 U.S.C. 154(b) by 240 days.

(21) Appl. No.: 13/387,297

(22) PCT Filed: Jul. 28, 2010

(86) PCT No.: PCT/GB2010/051236
§ 371 (c)(1),
(2), (4) Date: Jun. 7, 2012

(87) PCT Pub. No.: WO2011/012892
PCT Pub. Date: Feb. 3, 2011

(65) Prior Publication Data
US 2012/0245702 A1 Sep. 27, 2012

(30) Foreign Application Priority Data
Jul. 28, 2009 (GB) .................................. 0913137.6

(51) Int. Cl.
*A61F 2/34* (2006.01)
*A61F 2/30* (2006.01)
(Continued)

(52) U.S. Cl.
CPC ............... *A61F 2/34* (2013.01); *A61F 2/30734* (2013.01); *A61B 17/1666* (2013.01); *A61B 17/86* (2013.01); *A61F 2002/30192* (2013.01); *A61F 2002/30355* (2013.01); *A61F 2002/30387* (2013.01); *A61F 2002/30433* (2013.01); *A61F 2002/30449* (2013.01); *A61F 2002/30507* (2013.01); *A61F 2002/30512* (2013.01); *A61F 2002/30537* (2013.01); *A61F 2002/30553* (2013.01);
(Continued)

(58) Field of Classification Search
CPC ............... A61F 2/32; A61F 2/34; A61F 2/36; A61F 2220/0025; A61F 2002/3401; A61F 2/4609; A61F 2002/3408; A61F 2002/3429–2002/3437
USPC ........................ 623/22.11–22.39, 22.2, 22.42
See application file for complete search history.

(56) References Cited

U.S. PATENT DOCUMENTS

| 4,792,337 A | 12/1988 | Muller |
| 2002/0042654 A1 | 4/2002 | Masini |

(Continued)

FOREIGN PATENT DOCUMENTS

| EP | 0265712 A1 | 5/1988 |
| WO | WO-2006/031911 A2 | 3/2006 |

OTHER PUBLICATIONS

International Search Report for PCT/GB2010/051236, mailed Nov. 9, 2010; ISA/EP.

*Primary Examiner* — Christopher D Prone
(74) *Attorney, Agent, or Firm* — Harness, Dickey (57) ABSTRACT

A prosthetic assembly comprising: a body portion; first and second flanges provided on a rim of the body portion; the first and second flanges being provided with first and second openings respectively; and a bridging member connectable to the first and second flanges such that the member spans between the first and second flanges, the member being provided with a third opening; wherein the first, second and third openings are suitable for receiving first, second and third bone attachment members respectively.

25 Claims, 8 Drawing Sheets

(51) Int. Cl.
 A61B 17/16 (2006.01)
 A61B 17/86 (2006.01)
 A61F 2/46 (2006.01)
(52) U.S. Cl.
 CPC ........... *A61F2002/30578* (2013.01); *A61F 2002/30729* (2013.01); *A61F 2002/30736* (2013.01); *A61F 2002/30787* (2013.01); *A61F 2002/30797* (2013.01); *A61F 2002/30904* (2013.01); *A61F 2002/3417* (2013.01); *A61F 2002/3432* (2013.01); *A61F 2002/3469* (2013.01); *A61F 2002/4631* (2013.01); *A61F 2220/005* (2013.01); *A61F 2220/0025* (2013.01); *A61F 2220/0033* (2013.01); *A61F 2220/0041* (2013.01); *A61F 2230/0041* (2013.01); *A61F 2250/0004* (2013.01); *A61F 2250/0008* (2013.01)

(56) References Cited

U.S. PATENT DOCUMENTS

2006/0058887 A1* 3/2006 DeSmet et al. ............ 623/22.36
2007/0250175 A1 10/2007 Meridew et al.
2008/0262627 A1 10/2008 DeSmet et al.

* cited by examiner

PROSTHETIC ASSEMBLY

CROSS-REFERENCE TO RELATED APPLICATIONS

This application is a 371 U.S. National Stage of International Application No. PCT/GB2010/051236, filed Jul. 28, 2010. This application claims priority to Great Britain Patent Application No. GB-0913137.6, filed Jul. 28, 2009. The disclosures of the above applications are incorporated herein by reference.

FIELD

This invention relates to a prosthetic assembly and particularly but not exclusively relates to a prosthetic assembly with one or more openings, which are adapted to receive attachment members for attaching the prosthesis to bone.

BACKGROUND

A natural hip joint may undergo degenerative changes due to a variety of etiologies. When these degenerative changes become far advanced and irreversible, it may ultimately become necessary to replace a natural hip joint with a prosthetic hip. When implantation of such a hip joint prosthesis becomes necessary, the head of the femur, the acetabular, or both may need to be replaced. The head of the natural femur is first resected and a cavity is created within the intramedullary canal of the host femur for accepting the hip prosthesis. The hip prosthesis may be inserted and supported within the host femur by cementing the hip prosthesis within the host femur. Alternatively, the hip prosthesis may be impacted into the host femur so that it is a snug fit and supported by the host femur. In a further alternative, the femur may also be resurfaced, in which case the head is not resected. If the acetabulum also needs repair, all remnants of articular cartilage are generally removed from the acetabulum and an acetabular prosthesis which will accommodate the head or ball of the hip prosthesis is affixed to the acetabulum. The acetabular prosthesis is affixed to the acetabulum by means of cement, screws, an uncemented press fit or other appropriate fixation means.

Due to any number of reasons, however, a small portion of patients that undergo such orthopaedic surgical procedures may require subsequent revision surgery to replace the prosthetic device with a new prosthetic device generally referred to as a revision prosthesis.

In this regard, a revision acetabular prosthesis will generally include additional mounting points, such as integral extension members or hooks that provide additional stability for the revision acetabular prosthesis. These additional mounting points are generally required due to additional bone loss or defects exhibited at the acetabulum, such as collar/rim defects or pelvic discontinuity defects.

Various types of revision acetabular prostheses are currently available and different surgeons prefer different types of revision acetabular prostheses. Some surgeons prefer to use what is known as an Ilium flange that is formed integral with the acetabular prosthesis and enables further securement of the acetabular prosthesis in the Ilium region of the pelvis. Other surgeons prefer to use what is known as an obturator hook that is able to provide inferior fixation of the acetabular prosthesis by engaging the obturator foramen which is a large aperture adjacent the acetabulum. Because of this, a hospital must maintain a large inventory of different revision acetabular cups to meet the various surgeons' preferences. Moreover, the surgeon generally requires several revision acetabular cups available during surgery to account for any type of condition that may arise during the surgical procedure. Furthermore, as it may be desirable to have asymmetric securement to the acetabulum, left and right-handed revision acetabular cups may also be required.

This increased inventory of prosthetic devices increases the overall hospital costs and inventory control. Furthermore, by requiring the multiple revision acetabular cups to be available during the surgical procedure, multiple tools for the prosthetic devices may be required and these must be sterilized prior to the surgical procedure, thereby increasing the surgical time, cost and complexity. The present embodiments therefore seek to address these issues.

SUMMARY

According to a first aspect, there is provided a prosthetic assembly comprising: a body portion; first and second flanges provided on a rim of the body portion; the first and second flanges being provided with first and second openings respectively; and a bridging member connectable to the first and second flanges such that the member spans between the first and second flanges, the member being provided with a third opening; wherein the first, second and third openings are suitable for receiving first, second and third bone attachment members respectively.

The first opening may be disposed such that the first bone attachment means, once received in the first opening, may be orientated in a first plane containing a centreline of the body portion. The second opening may be disposed such that the second bone attachment member, once received in the second opening, may be orientated in a second plane containing a centreline of the body portion.

The first and/or second openings may be disposed such that the axes of the first and/or second openings may be angled in the range of substantially +60 to substantially −60 degrees with respect to the centreline of the body portion. The first and/or second openings may be disposed such that the axes of the first and/or second openings may be angled at substantially +20 or −20 degrees with respect to the centreline of the body portion.

The third opening may be disposed such that the third bone attachment member, once received in the third opening, may be oblique to a third plane containing a centreline of the body portion and the third opening. In addition to the third, fourth and fifth openings, the bridging member may comprise further openings for receiving further bone attachment members.

The bridging member may comprise fourth and fifth openings. The fourth opening may be disposed so as to overlap the first opening of the first flange and the fifth opening may be disposed so as to overlap the second opening of the second flange. The fourth and fifth openings may be disposed such that the first bone attachment member, once received in the first opening, may pass through the fourth and first openings and the second bone attachment member, once received in the second opening, may pass through the fifth and second openings. The first and second bone attachment members may be capable of securing the bridging member to the first and second flanges. Alternatively, the bridging member may be secured to the first and second flanges by first and second securing members, for example screws, which pass through the fourth and fifth openings respectively. The first and second securing members may pass into the first and second openings respectively. The first and second securing members may not pass into the bone.

The body portion may comprise a recess to receive an auxiliary bone engaging component. The auxiliary bone engaging component may comprise at least one of a compression screw, an Iliac plate, an Ischial blade, an Obturator hook and an augment.

The body portion may comprise an acetabular cup. The body portion may be a monoblock. The body portion may comprise a bearing surface, and as such the body portion may form a first bearing component, which may be configured to receive and cooperate with a second bearing component, for example the head of a femur.

Alternatively, the body portion may comprise a fixation element which may be fixedly attached to another element, for example as part of a shoulder, knee or spinal prosthetic. The body portion may not require a separate liner for engagement with the second bearing component. Nevertheless, a liner may be inserted between the body portion and the second bearing component Furthermore, the body portion and/or second bearing component may comprise a coating, for example a ceramic or diamond coating.

At least one of the first and second flanges may be angled with respect to the rim of the body portion. At least one of the first and second flanges may be provided with securing members for securing a drill guide to the first and/or second flange. The bridging member may be provided with further securing members for securing a further drill guide to the bridging member.

According to a second aspect there is provided a kit of parts for a prosthesis, the kit of parts comprising: a body portion; first and second flanges provided on a rim of the body portion; the first and second flanges being provided with first and second openings respectively; and a first bridging member connectable to the first and second flanges such that the first bridging member spans between the first and second flanges, the first bridging member being provided with a third opening; wherein the first, second and third openings are suitable for receiving first, second and third bone attachment members respectively.

The third opening may be disposed such that the third bone attachment member, once received in the third opening, may be oblique to a third plane containing a centreline of the body portion and the third opening.

The kit of parts may further comprise a second bridging member connectable to the first and second flanges such that the second bridging member may span between the first and second flanges. The second bridging member may be provided with a sixth opening suitable for receiving the third bone attachment member. The sixth opening may be disposed such that the third bone attachment member, once received in the sixth opening, may be oblique to the third plane in a direction opposite to that of the third opening of the first bridging member. In other words, the first and second bridging members may correspond to left- and right-handed bridging members, which are the mirror image of one another.

The kit of parts may further comprise at least one of a compression screw, a locking screw, a screw plate (e.g. an Iliac plate), a fixation blade (e.g. an Ischial blade), a hook (e.g. an Obturator hook) and an augment. The kit of parts may further comprise at least one drill guide for attachment to at least one of the first flange, second flange, first bridging member and second bridging member.

According to a third aspect there is provided a method of installing a prosthetic assembly, the method comprising: providing a body portion with first and second flanges provided on a rim of the body portion; the first and second flanges being provided with first and second openings respectively; connecting a first bridging member to the first and second flanges such that the first bridging member spans between the first and second flanges, the first bridging member being provided with a third opening; and affixing the prosthetic assembly to a bone by passing a third bone attachment member through the third opening. The method may further comprise affixing the prosthetic assembly to the bone by passing one or more of first and second bone attachment members through the first and second openings respectively.

According to a fourth aspect here is provided a hook for a prosthetic acetabular cup, wherein the hook comprises one or more gripping elements adapted to grip a portion of the pelvic obturator. The gripping elements may comprise a saw-tooth arrangement, for example with a repeating right-angled triangular cross-section, which may engage with the obturator.

The hook may comprise a first hole for receiving a screw to secure the hook to the prosthesis. The hook may be shaped so as to curve back on itself like a fish hook and may comprise a curved back portion. The hook may comprise a second hole which may be located on the curved back portion. The second hole may be opposite the first hole. Accordingly, the second hole may permit a tool to pass through the curved back portion so as to be able to access the screw which may be received in the first hole.

BRIEF DESCRIPTION OF THE DRAWINGS

For a better understanding of the present embodiments, and to show more clearly how it may be carried into effect, reference will now be made, by way of example, to the following drawings, in which.

DETAILED DESCRIPTION

Figure 1:
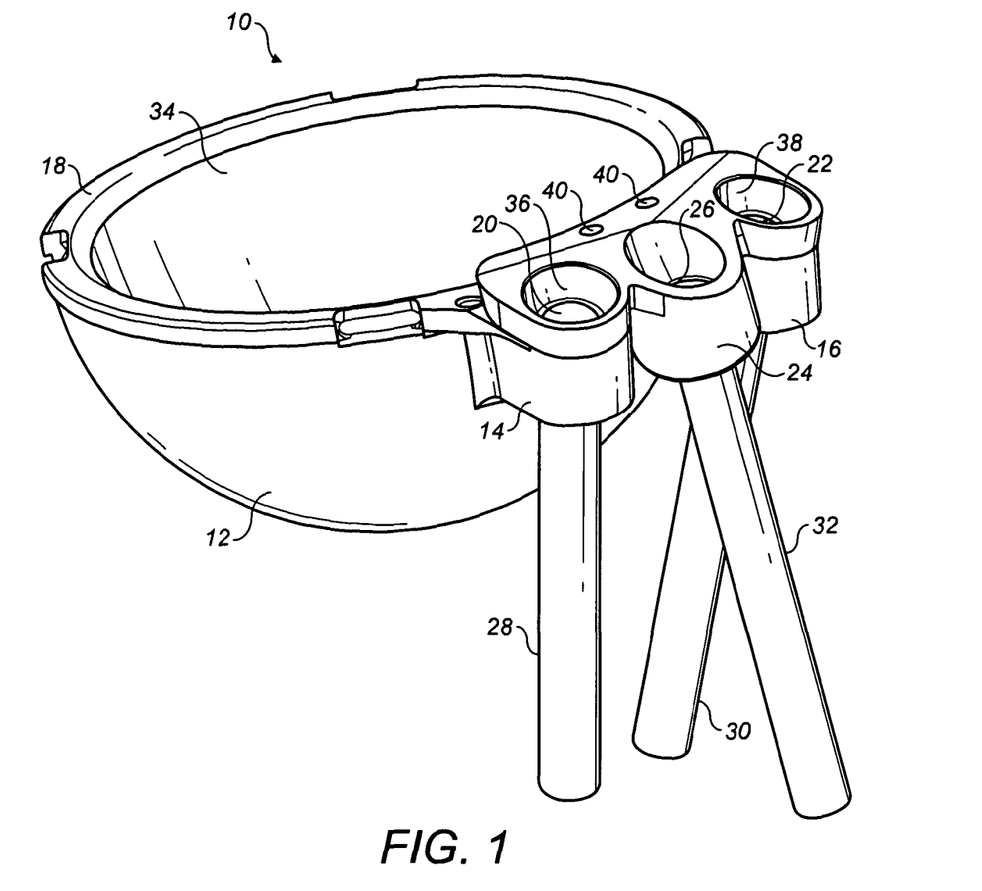
FIG. 1 shows a prosthetic assembly according to a first embodiment.

With reference to FIG. 1, a prosthetic assembly 10 according to a first embodiment comprises a body portion 12 in the form of a substantially hemispherical acetabular cup and first and second flanges 14, 16 provided on a rim 18 of the body portion 12. The first and second flanges 14, 16 are provided with first and second openings 20, 22 respectively. The prosthetic assembly 10 further comprises a bridging member 24 connectable to the first and second flanges 14, 16 such that the member 24 spans between the first and second flanges. The member 24 is provided with a third opening 26. The first, second and third openings 20, 22, 26 are suitable for receiving first, second and third bone attachment members or means 28, 30, 32 respectively for securing the prosthetic assembly 10 to a bone, for example the acetabulum. The bone attachment members may for example comprise bone attachment pins or screws. The first, second and/or third openings may be threaded bores and may for example be threaded to receive a threaded bone screw.

The body portion 12 is substantially hemispherical and the rim 18 corresponds to a great circle of the hemisphere. In other words, the rim 18 is within a plane which cuts through the centre of the sphere that defines the hemisphere. The body portion 12 comprises a bearing surface 34, and as such the body portion 12 may form a first bearing component, which is configured to receive and cooperate with a second bearing component (not shown), for example the head of a femur. Alternatively, the body portion 12 may comprise a fixation element which is fixedly attached to another element, for example as part of a shoulder, knee or spinal prosthetic. However, the body portion 12 of the present embodiment is a monoblock acetabular cup. As such the body portion 12 does not require a separate liner for engagement with the second bearing component. Nevertheless, a liner may be inserted between the body portion 12 and the second bearing component. Furthermore, the body portion and/or second bearing component may comprise a coating, for example a ceramic or diamond coating.

The first opening 20 is disposed such that an axis of the first opening is orientated in a first plane containing a centreline of the body portion 12. The axis of the first opening is coincident with the longitudinal axis of the first bone attachment member in the case of a straight bone attachment member. Similarly, the second opening 22 is disposed such that an axis of the second opening is orientated in a second plane containing a centreline of the body portion. The axis of the second opening is coincident with the longitudinal axis of the second bone attachment member in the case of a straight bone attachment member.

One or more of the first and second openings 20, 22 are configured such that one or more of the first and second bone attachment members 28, 30, once received in the first and/or second opening, are angled towards the centreline of the body portion 12 so as to intersect the centreline above or below the centre of the body portion. (Above and below relate to the orientation of the body portion shown in FIGS. 1 to 3.) The first and/or second openings may be disposed such that the axes of the first and/or second openings may be angled in the range of substantially +60 to substantially −60 degrees with respect to the centreline of the body portion. (Positive angles relate to an intersection of the axes with the centreline above the centre of the body portion, whilst negative angles relate to an intersection of the axes with the centreline below the centre of the body portion.) In particular, the first and/or second openings may be disposed such that the axes of the first and/or second openings may be angled at substantially +20 or substantially −20 degrees with respect to the centreline of the body portion. The first and second bone attachment members 28, 30 may be at the same angle such that the centreline of the body portion 12 and the axes of the first and second bone attachment members 28, 30 converge on a single point. Furthermore, the first and/or second openings may be disposed such that the axes of the first and/or second openings may be orientated cranially into the antero-superior part of the Ilium.

The outer faces of the first and/or second flanges 14, 16 are angled with respect to the plane containing the rim 18 of the body portion 12. (The outer face being the face of the first or second flange which does not face the bone.) The angle of the outer face may correspond to the angle of the bone attachment member with respect to the centreline of the body portion 12. For example, the outer face of the first and/or second flange may be at 20 degrees with respect to the rim 18. Furthermore, the outer faces of the first and/or second flanges may have features or shapes, which may interact with corresponding features or shapes in the bridging member. The features or shapes may provide additional fixation stability to the bridging member.

The third opening 26 is disposed such that the third bone attachment member 32, once received in the third opening, is oblique to a third plane containing a centreline of the body portion 12 and the third opening 26. Accordingly, the third bone attachment member 32 does not converge on the centreline of the body portion 12 and the third bone attachment means 32 diverges away from the first and second bone attachment members 28, 30. Alternatively, the third opening may be disposed such that the third bone attachment means may converge on the centreline of the body portion 12. The third bone attachment member 32 therefore secures the prosthetic assembly to a different region of bone. The third bone attachment member 32 also secures the body portion 12 in a different direction. The body portion 12 is therefore prevented from coming loose due to the failure of bone in one region or a force in a particular direction.

In addition to the third opening 26, the bridging member 24 further comprises fourth and fifth openings 36, 38. Once the bridging member 24 is installed, the fourth opening 36 is disposed so as to overlap the first opening 20 of the first flange 14 and the fifth opening 38 is disposed so as to overlap the second opening 22 of the second flange 16. The fourth and fifth openings 36, 38 are disposed such that the first bone attachment member 28, once received in the first opening 20, passes through the fourth and first openings. Similarly, the second bone attachment member 30, once received in the second opening 22, passes through the fifth and second openings. The first and second bone attachment members 28, 30 may be capable of securing the bridging member 24 to the first and second flanges, for example by virtue of a head portion. The head portion may abut the fourth or fifth openings in the bridging member 24 and hold the bridging member 24 and first or second flange 14, 16 between the head portion of the first or second bone attachment member and the bone. Alternatively, the head portion of the first or second bone attachment member may abut the first or second flange 14, 16. A head portion of the third bone attachment member 32 abuts the third openings 26 in the bridging member 24 and secures the bridging member 24, and hence the prosthetic assembly 10, to the bone. In a further alternative, the bridging member may be secured to the first and second flanges by first and second securing members or means, for example screws, which pass through the fourth and fifth openings respectively. The first and second securing members may pass into the first and second openings respectively. The first and second securing members may not pass into the bone.

The bridging member 24 is provided with further securing structures or means 40 in the form of bores for securing a drill guide to the bridging member. The bores may be blind bores and may also be threaded.

Figure 2:
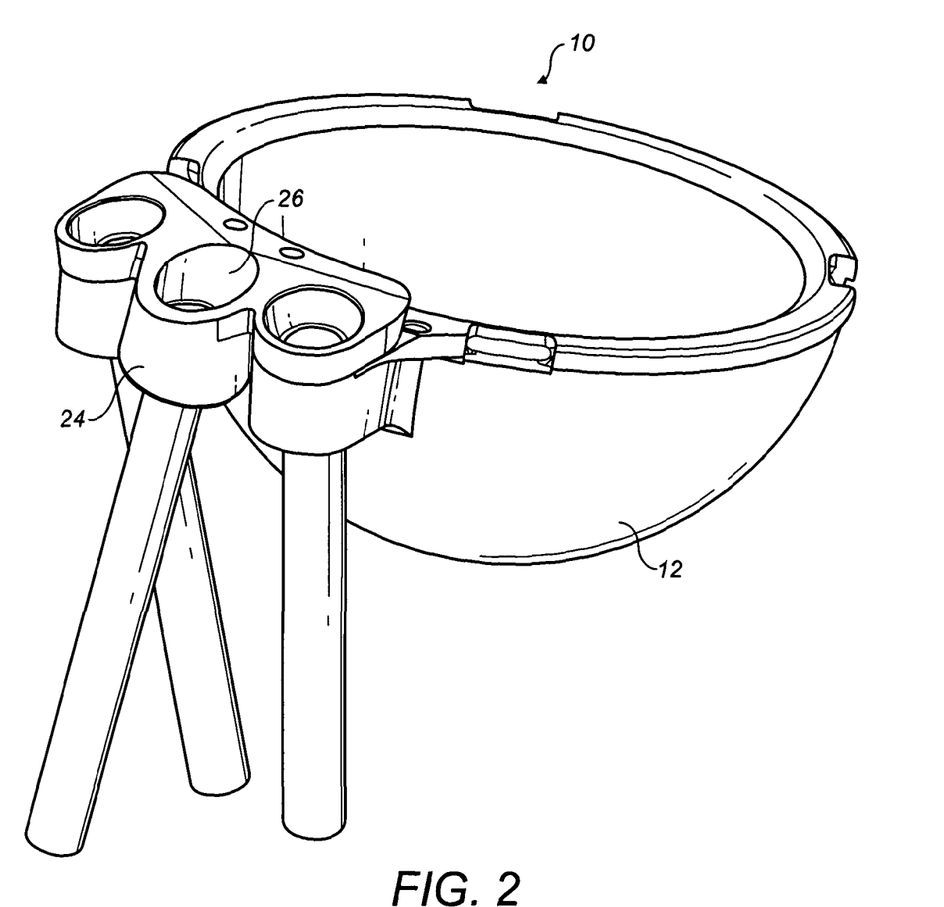
FIG. 2 shows a prosthetic assembly according to a second embodiment.

With reference to FIG. 2 a prosthetic assembly 10 according to a second embodiment of the invention comprises a mirror image of the bridging member 24 of the first embodiment such that the third opening 26 is angled in the opposite direction to that of the first embodiment. The second embodiment is otherwise substantially the same as the first embodiment. In this way, the first and second embodiments cater for both sides of the patient. Alternatively, the bridging member may receive a pivoting bone attachment member in the third opening and as such the same bridging member may be suitable for both sides of the patient. Accordingly, the third opening may be orientated such that an axis of the third opening may converge on the centreline of the body portion 12.

Figure 3A:
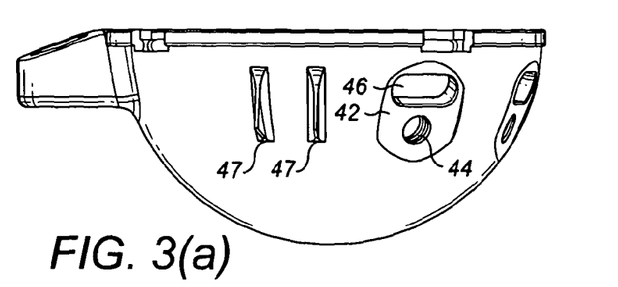
FIGS. 3(a)-(e) show recesses (FIGS. 3(a)-(b)) and auxiliary bone engaging components (FIGS. 3(c)-(e)) for the prosthetic assembly.
Figure 3B:
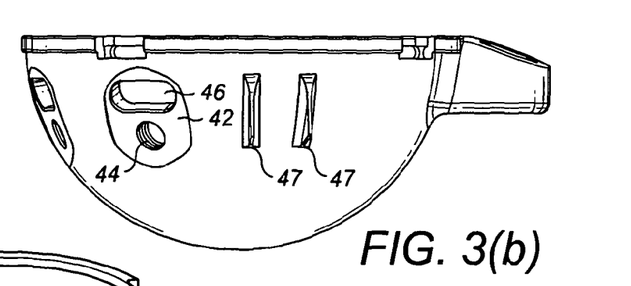

With reference to FIGS. 3(a)-(b), the body portion 12 of the first and second embodiments of the present invention comprises one or more recessed regions 42 to receive an auxiliary bone engaging component. The auxiliary bone engaging component may comprise a face shaped to cooperate with the shape of the recessed regions 42. The recessed regions 42 further comprise a bore 44 and a slot 46. The bore 44 may be threaded to receive a screw for securing the auxiliary bone engaging component to the body portion 12. The slot 46 may receive a cooperating protrusion on the auxiliary bone engaging component. The slot 46 and cooperating protrusion are obround shaped (i.e. a rectangular with semicircles at either end). The slot 46 and cooperating protrusion may be any other shape which assists in limiting rotation and movement of the auxiliary bone engaging component with respect to the body portion 12.

The body portion 12 further comprises fins 47 disposed about the bone facing surface of the body portion. The fins 47 may be substantially oblong and may be substantially orientated in a plane containing the centreline of the body portion 12.

Figure 3C:
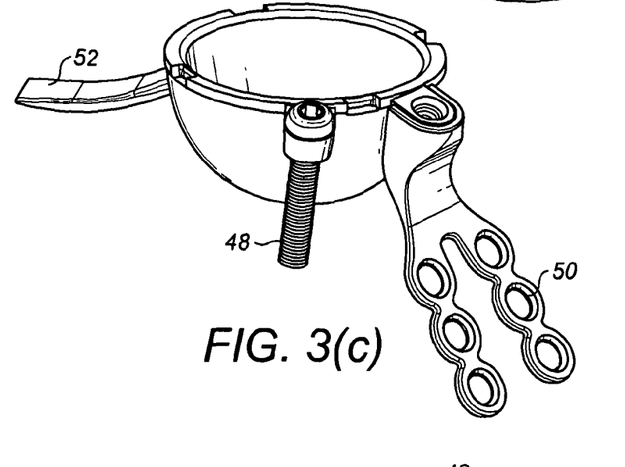
Figure 3D:
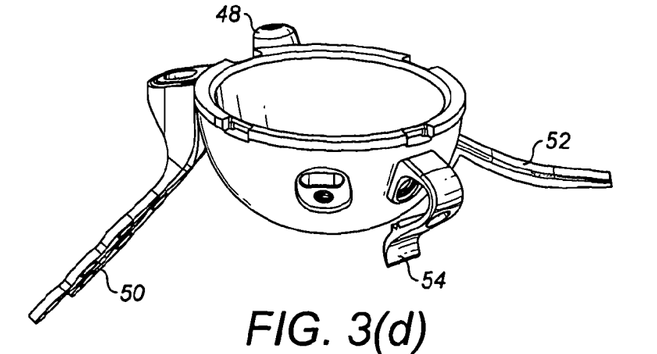
Figure 3E:
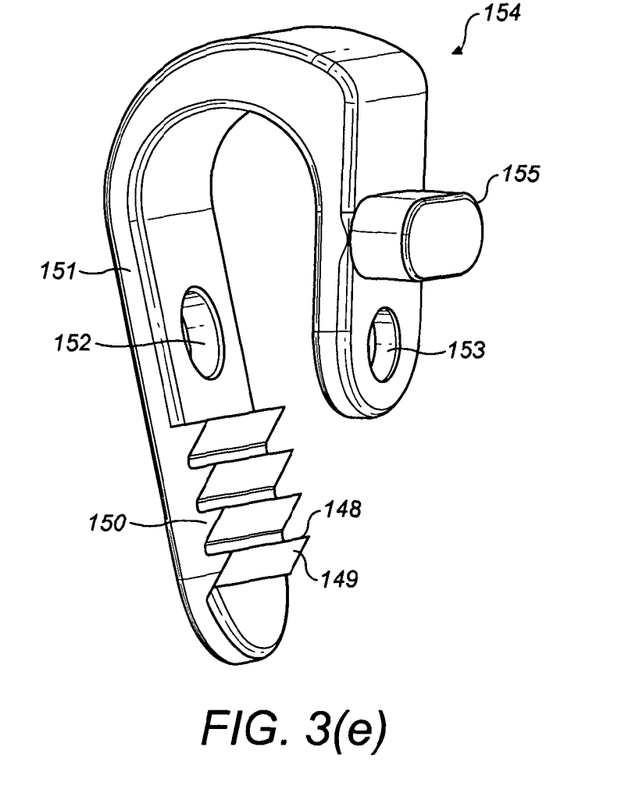

With reference to FIGS. 3(c)-(e), the auxiliary bone engaging component comprises at least one of a compression screw 48, an Iliac plate 50, an Ischial blade 52 and an Obturator hook 54. The auxiliary bone engaging component may further comprise a locking screw. The outside of the first and/or second flanges 14 and 16 may be tapered, and the Iliac plate 50 may comprise one or more corresponding tapered recesses to fit the first and/or second flanges.

An example of an Obturator hook 154 is shown in FIG. 3(e). The Obturator hook 154 comprises a protruding part 155 which is adapted to fit inside slot 46. The Obturator hook 154 further comprises a first hole 153 for receiving a screw to secure the Obturator hook into bore 44 of the prosthetic assembly 10. The Obturator hook is shaped so as to curve back on itself like a fish hook and accordingly comprises a curved back portion 151. The Obturator hook comprises a second hole 152 which is located on the curved back portion 151 and opposite the first hole 153. The second hole 152 permits a tool to pass through the curved back portion so as to be able to access the screw which is received in the first hole 153.

The Obturator hook 154 further comprises one or more gripping elements 150 on the curved back portion 151 which are adapted to grip the Obturator portion of the acetabulum. In particular, the gripping elements 150 may be in the form of a saw tooth arrangement, for example with a repeating right-angled triangular cross-section, which engages with the Obturator. The gripping elements 150 may comprise a ramped portion 149, which protrudes from the curved back portion 151, and a straight portion 148, which returns to the curved back portion 151 and is substantially perpendicular to the curved back portion. A sharp point is formed at the join between the ramped and straight portions 149, 148. The ramped and straight portions 149, 148 are orientated such that the ramped portion may ride over the Obturator bone portion during installation and that the sharp point defined at the join between the straight portion and ramped portion locks the Obturator hook 154 into place.

With reference to FIGS. 4(a)-(e), the prosthetic assembly 10 may further comprise an augment 56. The augment 56 may connect to the body portion 12 by virtue of the first and second flanges 14, 16. As such the bridging member 24 may be in the form of the augment 56 and the bridging member 24 may comprise the third, fourth and fifth openings 26, 36, 38 as described above. In other words the bridging member 24 may be in the shape of a bubble augment. The augment 56 may comprise one or more further openings in addition to the third, fourth and fifth openings 26, 36, 38, such that the augment may be attached to the body portion 12 in multiple positions about the circumference of the body portion. The augment 56 may further comprise first and second recess portions 58, 60 for receiving the first and second flanges 14, 16 respectively. The augment 56 may also comprise one or more of first, second and third bores 62, 63, 64, which may be oblique to the third, fourth and fifth openings and may also intersect the third, fourth and fifth openings. The first, second and third bores 62, 63, 64 may each comprise an abutment shoulder such that the augment 56 may be secured to the body portion 12 by virtue of screws.

Figure 4A:
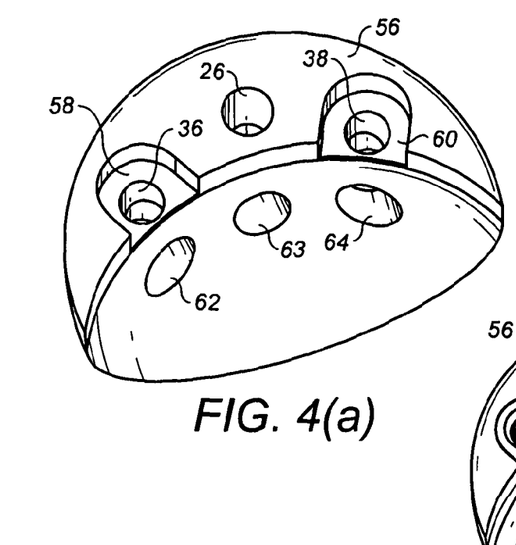
FIG. 4(a)-(e) show augments according to embodiments.
Figure 4B:
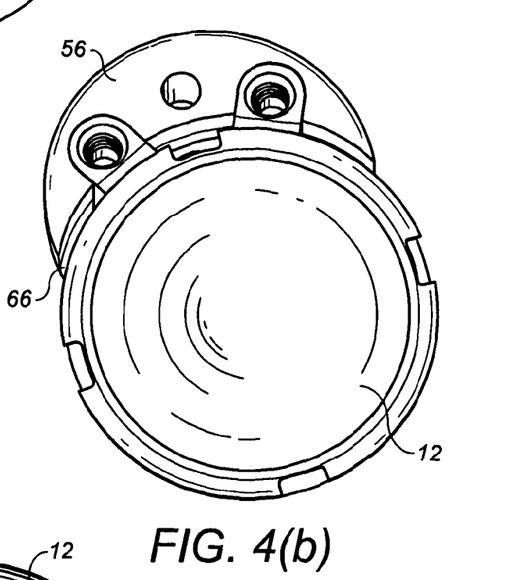
Figure 4C:
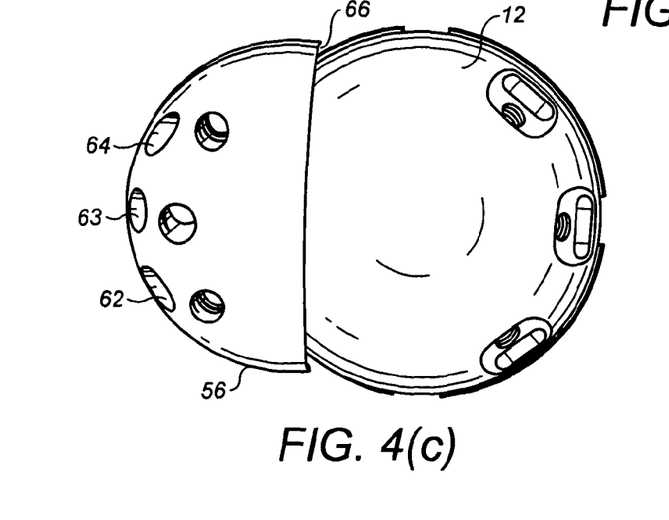
Figure 4D:
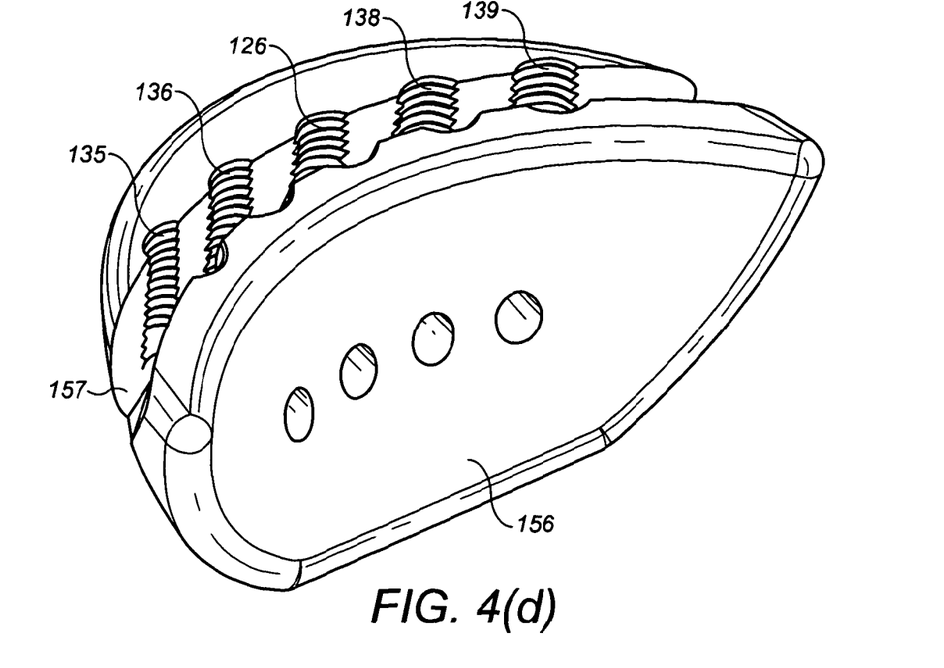
Figure 4E:
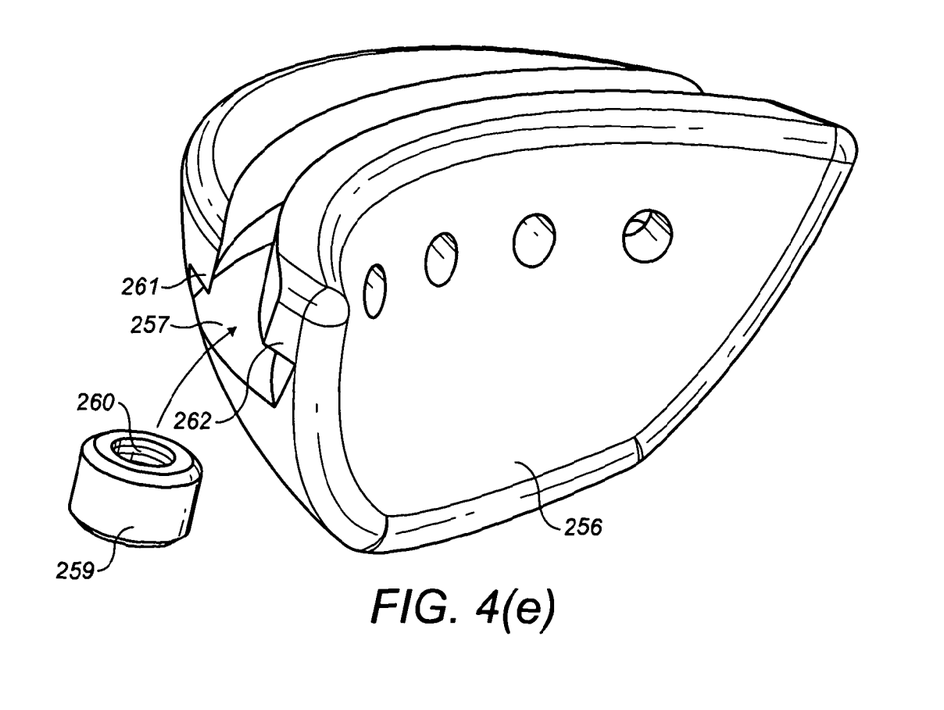

In an alternative arrangement shown in FIG. 4(d), an augment 156 may comprise a channel 157 intersecting the third, fourth and fifth openings 126, 136, 138 and the optional further openings 135 and 139. With the optional further openings, the augment may be attached to the body portion in multiple positions about the circumference of the body portion. In a further alternative arrangement shown in FIG. 4(e), an augment 256 may comprise a channel 257 with one or more shoulders 261, 262 which permit one or more adapters 259 to be slidably located within the channel. The adapters 259 comprise a threaded bore 260 for receiving threaded screws which also pass through the first and/or second openings 20, 22 of the first and second flanges 14, 16. As the screw is tightened, the adapter 259 engages the one or more shoulders 261, 262 and secures the augment 156 to the body portion 12. The augment 156 may be secured to the body portion in a range of orientations by sliding the one or more adapters 259 to a desired position within the channel 257.

The augment may be attached to the body portion 12 by virtue of one or more of the recessed regions 42 and the associated bore 44 and slot 46. The augment may not form the bridging member 24 and may be in addition to the bridging member. As such, the auxiliary bone engaging component may comprise an augment. There may be a plurality of recessed regions 42 such that the augment may be attached to the body portion 12 in multiple positions about the circumference of the body portion and in a range of orientations.

As shown in FIGS. 4(b)-(c), the augment 56 is attached to the body portion 12 in such a way that it leaves a gap 66 between the augment 56 and the body portion 12. The gap 56 allows for bone cement to penetrate between the augment and the body portion and provides a better fixation of the prosthetic assembly to the bone. The gap may be approximately 2 mm in width.

Figure 5A:
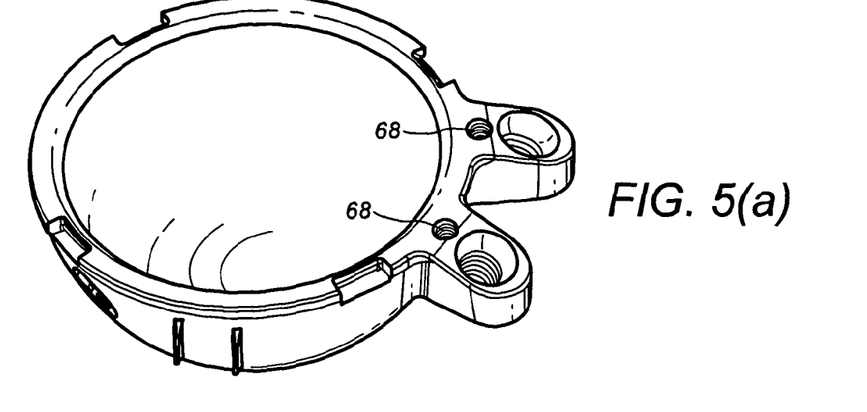
FIGS. 5(a)-(c) show the securing means (FIG. 5(a)) and drill guides (FIGS. 5(b) and 5(c)) for the prosthetic assembly.
Figure 5B:
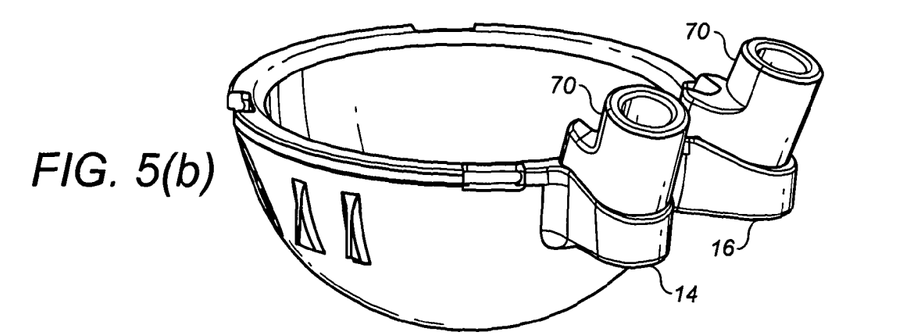
Figure 5C:
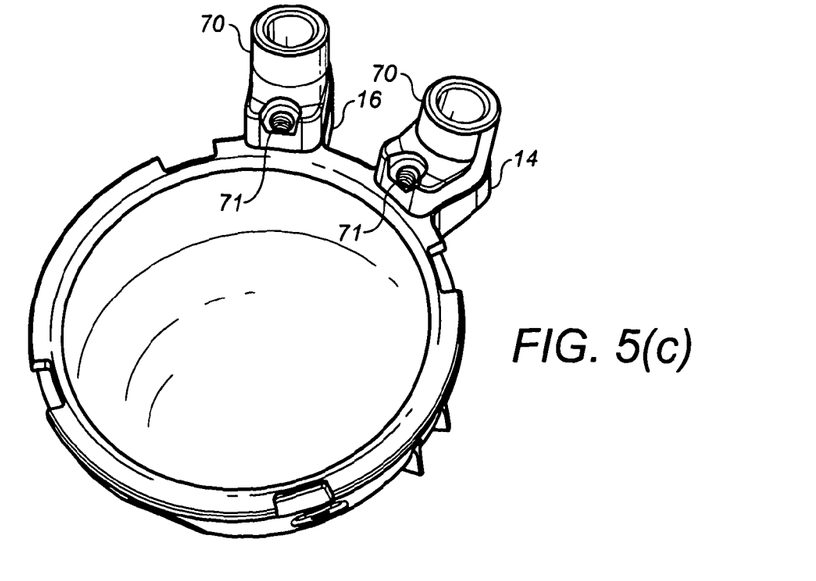

With reference to FIGS. 5(a)-(c) at least one of the first and second flanges may be provided with securing structures or means 68 in the form of bores for securing drill guides 70 to the first and/or second flange 14, 16. The securing structure 68 may also secure other instruments or bone attachment members to the first and/or second flange 14, 16. The bores may be blind bores and may also be threaded. FIG. 5(b) show the drill guides 70 secured to the first and second flanges 14, 16. The drill guides 70 may comprise openings (not shown) for receiving screws to secure the drill guides to the first and/or second flange. The drill guides 70 assist in guiding a drill into the bone so that a hole may be accurately drilled in a direction consistent with the orientation of the first and second openings 20, 22.

Figure 6A:
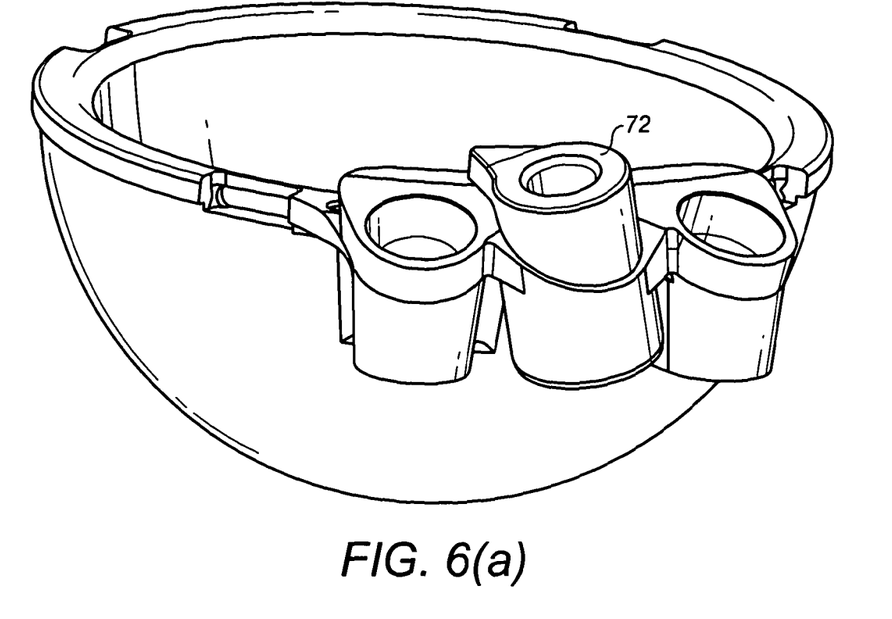
FIGS. 6(a) and 6(b) show the prosthetic assembly according to the first (FIG. 6(a)) and second (FIG. 6(b)) embodiments with a drill guide attached to the bridging member.
Figure 6B:
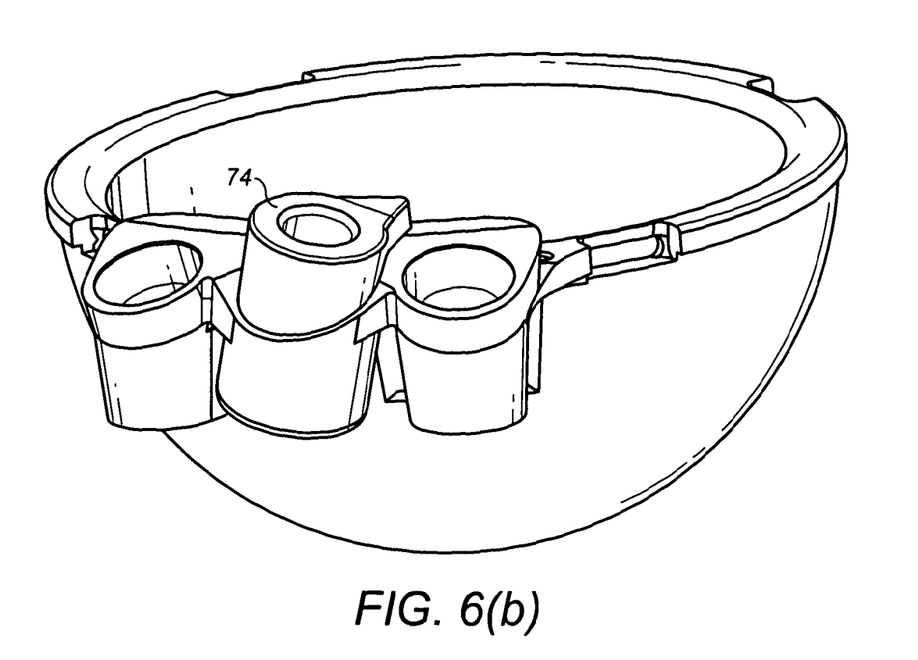

With reference to FIG. 6(a) a first angled drill guide 72 may be provided for engagement with the bridging member 24 of the first embodiment. Similarly, as shown in FIG. 6(b) a second angled drill guide 74 may be provided for engagement with the bridging member 24 of the second embodiment. The second angled drill guide 74 is a mirror image of the first angled drill guide 72. As for the drill guides 70, the angled drill guides 70 may comprise openings (not shown) for receiving screws to secure the drill guides to the securing structure 40 of the bridging member 24. The angled drill guides 72 assist in guiding a drill into the bone so that a hole may be accurately drilled in a direction consistent with the orientation of the third opening 26.

In terms of installation, the prosthetic assembly 10 may be implanted by first attaching the drill guides 70 to the first and second flanges 14, 16 and drilling holes into the bone. The drill guides 70 may be pre-attached to the first and second flanges 14, 16. The drill guides 70 are then removed and the appropriate bridging member 24 (depending on left or right hand side of patient) is lined up with the first and second flanges 14, 16 such that the first and second openings 20, 22 line up with the fourth and fifth openings 36, 38 respectively. The first and second bone attachment members 28, 30 (e.g. bone screws) are screwed through the first/fourth and second/fifth openings respectively and into the bone, thereby securing the bridging member 24 to the body portion 12 and the prosthetic assembly 10 to the bone. The appropriate angled drill guide 72, 74 is then secured to the bridging member 24 by virtue of the securing structure 40 and a third hole is drilled into the bone. Again, the angled drill guide 72, 74 may be pre-attached to the bridging member 24. Once the third hole has been drilled the angled drill guide is removed and the third bone attachment member 32 (e.g. bone screw) is screwed through the third opening 26 and into the bone.

In addition to the above, one or more of the aforementioned auxiliary bone engaging components may be attached to the body portion 12 prior to implantation of the prosthetic assembly 10.

The present invention minimizes the parts inventory by providing a universal body portion 12 which can be used on the left or right hand side of the patient. The body portion 12 can be subsequently configured for either side of the patient by the addition of left or right hand sided bridging members 24.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

The invention claimed is:

1. A prosthetic assembly comprising:
a body portion;
first and second flanges provided on the body portion; the first and second flanges being spaced apart to form a gap there between and provided with first and second openings respectively; and
a bridging member configured to span the gap and having third, fourth, and fifth openings and being connectable to the first and second flanges upon aligning the fourth and fifth openings with the first and second openings respectively with the third opening positioned at the gap; and
first, second, and third bone attachment members, wherein the third opening positioned at the gap is configured to receive the third bone attachment member, the first opening and the fourth opening are configured to receive the first bone attachment member, and the second opening and the fifth opening are configured to receive the second bone attachment member, such that, in use, the bridging member spans between the first and second flange and is connected to the first and second flanges by the first and second bone attachment members; and the prosthetic assembly is connected to bone by the first, second, and third bone attachment members.

2. The prosthetic assembly as claimed in claim 1, wherein the first opening is disposed such that an axis of the first opening is orientated in a first plane containing a centerline of the body portion.

3. The prosthetic assembly as claimed in claim 1, wherein the second opening is disposed such that an axis of the second opening is orientated in a second plane containing a centerline of the body portion.

4. The prosthetic assembly as claimed in claim 1, wherein one or more of the first and second openings are disposed such that axes of the first and/or second openings, are angled towards a centerline of the body portion.

5. The prosthetic assembly as claimed in claim 4, wherein the first and/or second openings are disposed such that the axes of the first and/or second openings are angled in a range of substantially +60 to substantially −60 degrees with respect to the centerline of the body portion.

6. The prosthetic assembly as claimed in claim 5, wherein the first and/or second openings are disposed such that the axes of the first and/or second openings are angled at substantially −20 degrees with respect to the centerline of the body portion.

7. The prosthetic assembly as claimed in claim 1, wherein the third opening is disposed such that an axis of the third opening, is oblique to a third plane containing a centerline of the body portion and the third opening.

8. The prosthetic assembly as claimed in claim 1, wherein the third opening is disposed such that an axis of the third opening is orientated in a third plane containing a centerline of the body portion.

9. The prosthetic assembly as claimed in claim 1, wherein the fourth opening being disposed so as to overlap the first opening of the first flange and the fifth opening being disposed so as to overlap the second opening of the second flange.

10. The prosthetic assembly as claimed in claim 9, wherein the first and second bone attachment members are configured to be screwed into the first and second openings respectively.

11. The prosthetic assembly as claimed in claim 1, wherein the body portion comprises a recess to receive an auxiliary bone engaging component.

12. The prosthetic assembly as claimed in claim 11, wherein the auxiliary bone engaging component comprises at least one of a compression screw, locking screw, a screw plate, a fixation blade, a hook and an augment.

13. The prosthetic assembly as claimed in claim 1, wherein the body portion comprises an acetabular cup.

14. The prosthetic assembly as claimed in claim 1, wherein the body portion comprises a monoblock.

15. The prosthetic assembly as claimed in claim 1, wherein at least one of the first and second flanges are angled with respect to a rim of the body portion.

16. The prosthetic assembly as claimed in claim 1, wherein at least one of the first and second flanges are configured to secure a drill guide to the first and/or second flange.

17. The prosthetic assembly as claimed in claim 1, wherein the bridging member is configured to secure a drill guide to the bridging member.

18. A kit of parts for a prosthesis, the kit of parts comprising:
- a body portion;
- first and second flanges provided on the body portion; the first and second flanges being spaced apart to form a gap there between and provided with first and second openings respectively; and
- a bridging member configured to span the gap and having third, fourth, and fifth openings and being connectable to the first and second flanges upon aligning the fourth and fifth openings with the first and second openings respectively with the third opening positioned at the gap; and
- first, second, and third bone attachment members, wherein the third opening positioned at the gap is configured to receive the third bone attachment member, the first opening and the fourth opening are configured to receive the first bone attachment member, and the second opening and the fifth opening are configured to receive the second bone attachment member, such that, in use the bridging member spans between the first and second flanges and is connected to the first and second flanges by the first and second bone attachment members and the prosthetic assembly is connected to bone by the first, second, and third bone attachment members.

19. The kit of parts for the prosthesis as claimed in claim 18, wherein the third opening is disposed such that an axis of the third opening is oblique to a third plane containing a centerline of the body portion and the third opening.

20. The kit of parts for the prosthesis as claimed in claim 19, wherein the kit of parts further comprises a second bridging member connectable to the first and second flanges such that the second bridging member spans between the first and second flanges, the second bridging member being provided with a sixth opening suitable for receiving the third bone attachment member; wherein the sixth opening is disposed such that an axis of the sixth opening is oblique to the third plane in a direction opposite to that of the third opening of the bridging member.

21. The kit of parts for the prosthesis as claimed in claim 18, wherein the third opening is disposed such that an axis of the third opening is orientated in a third plane containing a centerline of the body portion.

22. The kit of parts for the prosthesis as claimed in claim 18, further comprising at least one of a compression screw, a locking screw, a screw plate, a fixation blade, a hook and an augment.

23. The kit of parts for the prosthesis as claimed in claim 18, wherein the kit of parts further comprises at least one drill guide for attachment to at least one of the first flange, the second flange, and the bridging member.

24. A method of installing a prosthetic assembly, the method comprising:
- providing a body portion with first and second flanges provided on the body portion, the first and second flanges being spaced apart to form a gap there between and provided with first and second openings respectively;
- providing a bridging member, the bridging member being provided with third, fourth, and fifth openings;
- connecting the bridging member to the first and second flanges
- providing first, second, and third bone attachment members;
- affixing the bridging member to the first and second flanges by passing the first bone attachment member through the fourth opening into the first flange and passing the second bone attachment member through the fifth opening into the second flange; and
- affixing the prosthetic assembly to a bone by passing the first bone attachment member through the fourth opening into the first flange, passing the second bone attachment member through the fifth opening into the second flange, and by passing the third bone attachment member through the third opening into the bone, the third opening is positioned within the gap.

25. The method of installing a prosthetic assembly according to claim 24, wherein the method further comprises affixing the prosthetic assembly to the bone by screwing the first and second bone attachment members into the first and second openings respectively.

* * * * *